United States Patent [19]
Kuntsmann et al.

[11] Patent Number: 5,712,374
[45] Date of Patent: Jan. 27, 1998

[54] METHOD FOR THE PREPARATION OF SUBSTANTIALLLY MONOMERIC CALICHEAMICIN DERIVATIVE/CARRIER CONJUGATES

[75] Inventors: Martin P. Kuntsmann, Pearl River; Irwin Hollander, Monsey; Philip Hamann, Garnerville, all of N.Y.

[73] Assignee: American Cyanamid Company, Madison, N.J.

[21] Appl. No.: 475,005

[22] Filed: Jun. 7, 1995

[51] Int. Cl.$^6$ .................... C07K 16/00; A01N 43/04; C07G 11/00; C07H 15/00
[52] U.S. Cl. .................... 530/391.7; 530/391.1; 514/25; 514/53; 514/26; 536/16.8
[58] Field of Search .................... 530/391.1, 391.7, 530/391.5; 514/25, 26, 53; 536/16.8

[56] References Cited

U.S. PATENT DOCUMENTS

| | | | |
|---|---|---|---|
| 4,466,951 | 8/1984 | Pittman | 424/1.17 |
| 4,671,958 | 6/1987 | Rodwell et al. | 424/1.53 |
| 4,695,651 | 9/1987 | Marburg et al. | 560/1.41 |
| 4,970,198 | 11/1990 | Lee et al. | 514/25 |
| 5,028,697 | 7/1991 | Johnson et al. | 530/388.22 |
| 5,037,651 | 8/1991 | Lee et al. | 536/16.8 |
| 5,045,394 | 9/1991 | Uhr et al. | 428/402 |
| 5,053,394 | 10/1991 | Ellestad et al. | 514/25 |
| 5,079,233 | 1/1992 | Lee | 514/25 |
| 5,094,849 | 3/1992 | Cullinan et al. | 424/181.1 |
| 5,106,951 | 4/1992 | Morgan, Jr. et al. | 530/391.9 |
| 5,124,441 | 6/1992 | Carlsson et al. | 536/6.1 |
| 5,155,210 | 10/1992 | Wrasidlo | 530/317 |
| 5,160,723 | 11/1992 | Welt et al. | 424/155.1 |
| 5,225,539 | 7/1993 | Winter et al. | 530/387.3 |
| 5,431,897 | 7/1995 | Welt et al. | 424/1.49 |
| 5,461,068 | 10/1995 | Thaler et al. | 514/399 |

FOREIGN PATENT DOCUMENTS

| | | |
|---|---|---|
| 0132082 | 1/1985 | European Pat. Off. |
| 0208615 | 1/1987 | European Pat. Off. |
| 0313873 | 5/1989 | European Pat. Off. |
| 0392384 | 10/1990 | European Pat. Off. |
| 0040506 | 11/1991 | European Pat. Off. |
| 0689845 | 1/1996 | European Pat. Off. |
| WO91/09967 | 7/1991 | WIPO . |
| WO93/06231 | 4/1993 | WIPO . |
| WO94/13805 | 6/1994 | WIPO . |

OTHER PUBLICATIONS

The Merk Index (An encyclopedia of chemicals, drugs and biologicals) Tenth edition., Merk & Co., Inc., 1983, pp. 1130–1131.
Adam et al. Synthetic adjuvants, John Wiley & Sons 1985, pp. 137–138.
K.C. Nicolaou, et al., J. Am Chem. Soc., 110(14):4866–4868(1988).
Koppel, G., Recent Advances with Monoclonal Antibody Drug Targeting for the Treatment of Human Cancer, Bioconjugate Chem. 1990, 1, 13–23.
The Design of Cytotoxic–Agent–Antibody Conjugates, CRC Critical Reviews in Therapeutic Drug Carrier Systems, vol. 3, Issue 4, pp. 263–359 (1987).
Chemical Modification of Antibodies for Cancer Chemotherapy, Janis Upeslacis and Lois Hinman, Annual Reports in Medicinal Chemistry—23, pp. 151–160 (1988).
The Covalent Structure of a Human γG–Immunoglobulin. VI. Amino Acid Sequence of the Light Chain, Gottlieb et al., Biochemistry, vol. 9, No. 16, 1970, pp. 3135–3140.
The Covalent Structure of a Human γG–Immunoglobulin. VII. Amino Acid Sequence of the Heavy–Chain Cyanogen Bromide Fragments $H_1$–$H_4$, Biochemistry, vol. 9, No. 16, 1970, pp. 3161–3170.
Borreback, J. Immunol. Methods, 123: 157–165 (1989).
Waldmann, Science, 252: 1657–1662 (1991).
Osband et al., Immunology Today, 11:193–195 (1990).
Harris et al., TIBTECH, 11:42–44 (1993).
Dillman, Animals of Internal Med., vol. 111:592–603 (1989).
Bach et al., Immunology Today, 14:421–425 (1993).
Hermentin et al., Behring Inst. Mitt, No. 82, pp. 197–215 (1988).
Seaver, Genetic Engineering News, 14:10 and 21 (1994).
Hird, V., et al., Immunotherapy with Monoclonal Antibodies. In: Genes and Cancer, Carney et al. (ed.) Wiley & Sons, (1990).
Queen, C., et al., Proc. Natl. Acad. Sci, USA, 86:10029–10033 (1989).
Riechmann, L., et al., Nature, 332:323–327 (1988).
J. Amer. Chem. Soc., 110(14):4866–4868 (1988).
Kohler et al., Nature, 256:495–497 (1975).
Bernstein et al., J. Clin. Invest. 79:1153–1159 (1987).
Uchiyama et al., J. Immunol., 126:1393–1397 (1981).

*Primary Examiner*—Ponnathapura Achutamurthy
*Assistant Examiner*—P. Ponnaluri
*Attorney, Agent, or Firm*—Elizabeth M. Barnhard; Darby & Darby

[57] ABSTRACT

A method is provided for preparing monomeric calicheamicin derivative/carrier conjugates with higher drug loading/yield and decreased aggregation. These conjugates are prepared by incubating a calicheamicin derivative and a proteinaceous carrier in a solution comprising a phosphate buffered solution, a cosolvent comprising propylene glycol, an additive comprising at least one $C_6$–$C_{25}$ carboxylic acid, preferably having a pH in the range from about 7.0 to 8.5, and at a temperature ranging from about 25° C. to about 37° C. for a period of time ranging from about 2 hours to about 18 hours, and recovering monomeric calicheamicin derivative/carrier conjugates. Alternatively, the conjugates can be prepared by incubating the calicheamicin derivative and a proteinaceous carrier in a solution comprising a phosphate buffered solution and a cosolvent comprising t-butanol.

30 Claims, No Drawings

METHOD FOR THE PREPARATION OF SUBSTANTIALLLY MONOMERIC CALICHEAMICIN DERIVATIVE/CARRIER CONJUGATES

FIELD OF THE INVENTION

The present invention relates to methods for producing substantially monomeric calicheamicin derivative/carrier conjugates.

BACKGROUND OF THE INVENTION

Since the discovery of methodology for producing monoclonal antibodies was published in the 1970's (G. Köhler and C. Milstein, *Nature* 256:495 (1975)), numerous attempts have been made to use these proteins selectively to target antitumor agents to tumors. (E.g., see T. Ghose and A. H. Blair, *CRC Critical Rev. Drug Carrier Systems* 3:263, 1987, G. A. Koppel, *Bioconjugate Chem.* 1:13, 1990, and J. Upeslacis and L. Hinman, *Ann. Rep. Med. Chem.* 23:151, 1988.) Although progress continues to be made in this field, most classical antitumor agents produce antibody conjugates which are relatively ineffective for a variety of reasons. Among the reasons for this ineffectiveness is the lack of potency of the chemotherapeutic agent and its poor utilization due to inefficient release of the drug at its site of action.

The potent family of antibacterial and antitumor agents, known collectively as the calicheamicins or the LL-E33288 complex, are described in U.S. Pat. No. 4,970,198 (1990). The most potent of the agents is designated $\gamma_1^I$, which is herein referenced simply as gamma. These compounds contain a methyltrisulfide that can be reacted with appropriate thiols to form disulfides, at the same time introducing a functional group such as a hydrazide or similar nucleophile. Examples of this reaction with the calicheamicins are given in U.S. Pat. No. 5,053,394 which also discloses targeted forms of the calicheamicins.

A factor which has limited the use of the above-mentioned conjugates is that when the conjugation reactions are performed with calicheamicin and the linkers described in U.S. patent application Ser. No. 08/253,877, abandoned in the presence of dimethylformamide (DMF) or dimethylsulfoxide (DMSO), a large percentage (greater than 50%) of the conjugates produced are in an aggregated form that is unsuitable for further purification for therapeutic administration. Therefore, there is a need for methods for conjugating carriers to cytotoxic drugs which yield a substantially monomeric product and for such monomeric conjugates.

SUMMARY OF THE INVENTION

The conjugates of the present invention have the formula

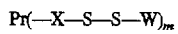

wherein:

Pr is a proteinaceous carrier,

X is a linker that comprises a product of any reactive group that can react with a proteinaceous carrier, W is the calicheamicin residue formed when a calicheamicin is cleaved at a methyltrisulfide linkage; and m is from 0.1 to 15.

DETAILED DESCRIPTION OF THE INVENTION

The conjugates of the present invention include a therapeutic agent derivatized with a linker that includes any reactive group that reacts with a proteinaceous targeting carrier. The use of particular cosolvents and additives induces the monomeric form as opposed to the aggregate form of these conjugates. The monomeric form has therapeutic value.

Carriers

The carriers of the present invention preferably are proteinaceous carriers. Included as carrier molecules are steroids, growth factors, antibodies, antibody fragments, and their genetically or enzymatically engineered counterparts, hereinafter referred to singularly or as a group as carriers. The essential property of the carrier is its ability to recognize an antigen or receptor associated with undesired cells. Examples of carriers are given in U.S. Pat. No. 5,053,394, and such carriers are also appropriate in the present invention. Preferred carriers for use in the present invention are human or humanized antibodies.

Specific examples of carriers which are exemplified herein are the antibodies P67.6, A33, CT-M-01 and the "anti-Tac" antibody of Waldman. These antibodies are used herein in two forms: a murine form, designated by an "m" (e.g., m-P67.6), and a genetically engineered, humanized form, designated by an "h" (e.g., h-P67.6) whenever appropriate. The basic technology for antibody humanization is disclosed by Winter in U.S. Pat. No. 5,225,539 (1993) and by Adair in PCT Publication NO. WO 91/09967 (1991). m-P67.6 is disclosed in L. D. Bernstein et al., *J. Clin. Invest.* 79:1153, 1987 and recognizes the CD33 antigen which is prevalent on certain human myeloid tumors, especially acute non-lymphocytic leukemia (ANLL).

U.S. patent application Ser. No. 08/253,877 filed Jun. 3, 1994, abandoned discloses the DNA coding and predicted amino acid sequences of the variable regions of one particular h-P67.6 that is particularly preferred for use in the present invention. The framework for this antibody is the EU framework for human IgG$_4$ shown in Gottlieb et al., *Biochemistry* 9:3115 and 3161, 1970. The antibody was prepared using the general strategy described in PCT Publication No. WO 91/09967.

The antibody m-CT-M-01 is disclosed in European Patent Application No. 86401482.4/0208615 and recognizes the polyepithelial mucin (PEM) antigen present on many human solid tumors, particularly breast, lung, and ovarian tumors. The humanized version of this antibody, h-CT-M-01, is described in PCT Publication No. WO 93/06231 (1993). The antibody m-A33 is disclosed in U.S. Pat. Nos. 5,160,723 and 5,431,897 and is a murine antibody which recognizes a glycoprotein antigen present on colon cancer cells. The humanized version of this antibody, h-A33, is disclosed in PCT Patent Publication No. W094/13805 (Jun. 23, 1994). Anti-Tac is disclosed in T. A. Waldman et al., *J. Immunol.* 126:1393, 1981 and is a murine antibody reactive with the IL-2 receptor that is found on activated and functionally mature T cells, including abnormally activated leukemia cells.

Therapeutic Agents

The therapeutic agents suitable for use in the present invention are cytotoxic antibiotics that bind to and disrupt DNA. Preferred cytotoxic agents are the calicheamicins which are methyl trisulfide antitumor antibiotics. Examples of calicheamicins suitable for use in the present invention are disclosed for example in U.S. Pat. No. 5,053,394. See also, U.S. Pat. Nos. 4,671,958; 4,970,198; 5,037,651; and 5,079,233. Preferred calicheamicins are gamma-calicheamicins. The structure of gamma-calicheamicin in a conjugated form is illustrated below.

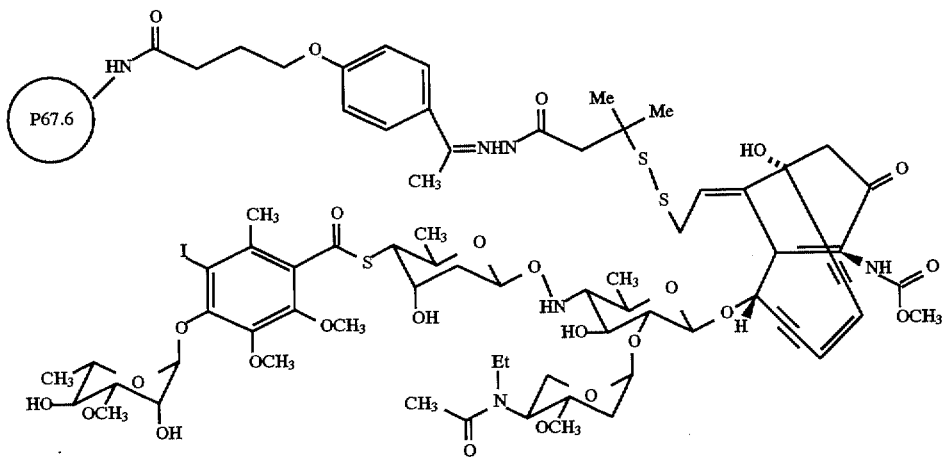

Calicheamicin Derivative/Carrier Conjugates

The conjugates of the present invention have the formula

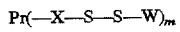

wherein:

Pr is a proteinaceous carrier,

X is a linker that comprises a product of any reactive group that can react with a proteinaceous carrier, W is the calicheamicin residue formed when a calicheamicin is cleaved at a methyltrisulfide linkage; and m is from 0.1 to 15.

Preferably, X has the formula Z—Sp wherein:

Sp is a straight or branched-chain divalent or trivalent ($C_1$–$C_{18}$) radical, divalent or trivalent aryl or heteroaryl radical, divalent or trivalent ($C_3$–$C_{18}$) cycloalkyl or heterocycloalkyl radical, divalent or trivalent aryl or heteroarylalkyl ($C_1$–$C_{18}$) radical, divalent or trivalent cycloalkyl- or heterocycloalkyl-alkyl ($C_1$–$C_{18}$) radical or divalent or trivalent ($C_2$–$C_{18}$) unsaturated alkyl radical, wherein if Sp is a trivalent radical, it can be additionally substituted by amino, alkylamino, arylamino, heteroarylamino, carboxyl, lower alkoxy, hydroxy, thiol, or lower alkylthio groups; and Z is —CONH—, —CONHN=CH—, —CONHNHCH$_2$—, —NHCONHN=CH—, —NHCONHNHCH$_2$, —NHCSNHN=CH—, —NHCH$_2$—, —N=CH—, —CO$_2$, —NHCH$_2$CO$_2$—, —SS—,

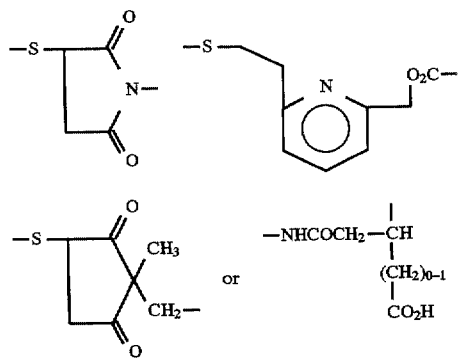

Alternatively, X has the formula (CO—AlK$^1$—Sp$^1$—Ar—Sp$^2$—AlK$^2$—C(Z$^1$)=Q—Sp)

wherein

Alk$^1$ and Alk$^2$ are independently a bond or branched or unbranched ($C_1$–$C_{10}$) alkylene chain;

Sp$^1$ is a bond, —S—, —O—, —CONH—, —NHCP—, —NR'—, —N(CH$_2$CH$_2$)$_2$N—, or —X—Ar'—Y—(CH$_2$)$_n$—Z wherein X, Y, and Z are independently a bond, —NR'—, —S—, or —O—, with the proviso that when n=0, then at least one of Y and Z must be a bond and Ar' is 1,2-, 1,3-, or 1,4-phenylene optionally substituted with one, two, or three groups of ($C_1$–$C_5$) alkyl, ($C_1$–$C_4$) alkoxy, ($C_1$–$C_4$) thioalkoxy, halogen, nitro, COOR', CONHR', O(CH$_2$)$_n$COOR', S(CH$_2$)$_n$COOR', O(CH$_2$)$_n$CONHR', or S(CH$_2$)$_n$CONHR', with the proviso that when Alk$^1$ is a bond, Sp$^1$ is a bond;

n is an integer from 0 to 5;

R' is a branched or unbranched ($C_1$–$C_5$) chain optionally substituted by one or two groups of —OH, ($C_1$–$C_4$) alkoxy, ($C_1$–$C_4$) thioalkoxy, halogen, nitro, ($C_1$–$C_3$) dialkylamino, or ($C_1$–$C_3$) trialkylammonium —A— where A— is a pharmaceutically acceptable anion completing a salt;

Ar is 1,2-, 1,3-, or 1,4-phenylene optionally substituted with one, two, or three groups of ($C_1$–$C_6$) alkyl, ($C_1$–$C_5$) alkoxy, ($C_1$–$C_4$) thioalkoxy, halogen, nitro, or COOR', CONHR', O(CH$_2$)$_n$COOR', S(CH$_2$)$_n$COOR', O(CH$_2$)$_n$CONHR', or S(CH$_2$)$_n$CONHR' wherein n and R' are as hereinbefore defined or a 1,2-, 1,3-, 1,5-, 1,6-, 1,7-, 1,8-, 2,3-, 2,6-, or 2,7-naphthylidene or

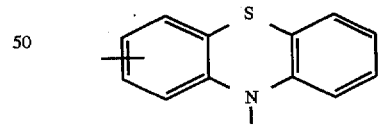

each naphthylidene or phenothiazine optionally substituted with one, two, three, or four groups of ($C_1$–$C_6$) alkyl, ($C_1$–$C_5$) alkoxy, ($C_1$–$C_4$) thioalkoxy, halogen, nitro, or COOR', CONHR', O(CH$_2$)$_n$COOR', S(CH$_2$)$_n$COOR', or S(CH$_2$)$_n$CONHR' wherein n and R' are as defined above, with the proviso that when Ar is naphthylidene, Z$^1$ is not hydrogen and with the proviso that when Ar is phenothiazine, Sp$^1$ is a bond only connected to nitrogen;

Sp$^2$ is a bond, —S—, or —O—, with the proviso that when Alk$^2$ is a bond, Sp$^2$ is a bond;

Z$^1$ is H, ($C_1$–$C_5$) alkyl, or phenyl optionally substituted with one, two, or three groups of ($C_1$–$C_5$) alkyl, ($C_1$–$C_5$)

alkoxy, ($C_1$–$C_4$) thioalkoxy, halogen, nitro, COOR', CONHR', O($CH_2$)$_n$COOR', S($CH_2$)$_n$COOR', O($CH_2$)$_n$CONHR', or S($CH_2$)$_n$CONHR' wherein n and R' are as above;

Sp is a straight or branched-chain divalent or trivalent ($C_1$–$C_{18}$) radical, divalent or trivalent aryl or heteroaryl radical, divalent or trivalent ($C_3$–$C_{18}$) cycloalkyl or heterocycloalkyl radical, divalent or trivalent aryl- or heteroarylaryl ($C_1$–$C_{18}$) radical, divalent or trivalent cycloalkyl- or heterocycloalkyl-alkyl ($C_1$–$C_{18}$) radical or divalent or trivalent ($C_2$–$C_{18}$) unsaturated alkyl radical, wherein heteroaryl is furyl, thienyl, N-methylpyrrolyl, pyridinyl, N-methylimidizolyl, oxazolyl, pyrimidinyl, quinolyl, isoquinolyl, N-methylcarbazoyl, aminocourmarinyl, or phenazinyl and wherein if Sp is a trivalent radical, Sp can be additionally substituted by lower ($C_1$–$C_5$) dialkylamino, lower ($C_1$–$C_5$) alkoxy, hydroxy, or lower ($C_1$–$C_5$) alkylthio groups; and Q is =NHNCO—, =NHNCS—, =NHNCONH—, =NHNCSNH—, or =NHO—.

Preferably, Sp' is a bond, —S—, —O—, —CONH—, —NHCO—, or —NR' wherein n and R' are as hereinbefore defined, with the proviso that when $Alk^1$ is a bond, $Sp^1$ is a bond;

Ar is 1,2 -, 1,3 -, or 1,4 -phenylene optionally substituted with one, two, or three groups of ($C_1$–$C_6$) alkyl, ($C_1$–$C_5$) alkoxy, ($C_1$–$C_4$) thioalkoxy, halogen, nitro, or COOR', CONHR', O($CH_2$)$_n$COOR', S($CH_2$)$_n$COOR', O($CH_2$)$_n$CONHR', or S($CH_2$)$_n$CONHR' wherein n and R' are as hereinbefore defined or Ar is a 1,2-, 1,3-, 1,4-, 1,5-, 1,6-, 1,7-, 1,8-, 2,3-, 2,6-, or 2,7- naphthylidene each optionally substituted with one, two, three, or four groups of ($C_1$–$C_6$) alkyl, ($C_1$–$C_5$) alkoxy, ($C_1$–$C_4$) thioalkoxy, halogen, nitro, or COOR', CONHR', O($CH_2$)$_n$COOR', S($CH_2$)$_n$COOR', O($CH_2$)$_n$CONHR', or S ($CH_2$)$_n$CONHR'.

$Alk^2$ is a branched or unbranched ($C_1$–$C_{10}$) alkylene chain;

$Z^1$ is $Z^1$ is phenyl optionally substituted with one, two, or three groups of ($C_1$–$C_5$) alkyl, ($C_1$–$C_4$) alkoxy, ($C_1$–$C_4$) thioalkoxy, halogen, nitro, COOR', CONHR', O($CH_2$)$_n$COOR', S($CH_2$)$_n$COOR', ($CH_2$)$_n$CONHR', or S($CH_2$)$_n$CONHR'; and $Alk^2$ and $Sp^2$ are together a bond.

Calicheamicin derivatives can, for example, attach to lysine residues of the antibody. Lysine attachment as disclosed in U.S. Pat. No. 5,053,394 produces conjugates which are stable to hydrolysis under normal physiological conditions.

U.S. patent application Ser. No. 08/253,877 filed Jun. 3, 1994, abandoned discloses other linkers that can be added to a derivative of a drug, particularly hydrazides and related nucleophiles, prepared from the methyltrisulfide containing antitumor antibodies.

The linkage formed between the drug and the linker must be a hydrolyzable linkage in order to release the drug at the proscribed site. Therefore, the linkers useful in practicing the subject invention are often compounds having two linking-functional groups. One group typically is an acid group that is utilized to react with the carrier. The acid functional group can form an amide linkage with a free amine group of the carrier, such as, for example, the amine in the side chain of a lysine of a monoclonal antibody carrier. Alternatively, the acid functional group can be reacted with an amine, alcohol, or other appropriate nucleophile on other targeting agents which have been chosen for their ability to target undesired cell populations.

The other linking-functional group commonly is a carbonyl group, i.e., an aldehyde or a ketone, which will react with the therapeutic agent. The carbonyl groups can react with a hydrazine group on the drug to form a hydrazone linkage. This linkage is hydrolyzable at the target cell to release the therapeutic agent from the conjugate.

A preferred linker for use in the present invention is 4(4(acetyl)phenoxy) butanoic acid (AcBut).

Special mention is made of the conjugate prepared with gamma-calicheamicin, the linker 4(4(acetyl)phenoxy) butanoic acid (AcBut), and a human monoclonal antibody targeting carrier.

Substantially Monomeric Conjugation

The increased hydrophobicity of the linkage provided by AcBut and other linkers such as, for example, those disclosed in U.S. patent application Ser. No. 08/253,877, abandoned possibly increased length separating a therapeutic agent from a MoAb carrier, combined with the natural hydrophobic nature of the therapeutic agent calicheamicin, created difficulties in the preparation of monomeric conjugates. Monomeric conjugates are necessary for clinical therapeutic applications.

Substantially monomeric conjugates of the present invention are conjugate mixtures in which at least about 50% of the conjugates are in non-aggregated form. Preferably at least about 75% are in non-aggregated form, and most preferably at least about 90% are in non-aggregated form. Substantially monomeric conjugates can be formed with a high drug loading, i.e. about 4 to about 5 mM.

Prior to the present invention, conditions for conjugating, for example, N-hydroxy-succinimide ester (O—Su) derivatized calicheamicins utilized dimethyl formamide (DMF) as a cosolvent. These conditions produced poor monomer yields and drug loadings with AcBut-calicheamicin conjugations. For the development of conjugates for clinical use, yields of monomeric conjugate of at least 50% with drug loading of ~2 moles drug per mole MoAb are preferably obtained.

For humanized carriers including, but not limited to, proteins such as human or humanized monoclonal antibodies that are used to target the cytotoxic therapeutic agents herein, such as, for example, P67.6 and the other humanized monoclonal antibodies disclosed herein, the use in PBS of (i) propylene glycol (PG), t-butanol, or a combination thereof as a cosolvent and (ii) optionally, at least one $C_6$–$C_{25}$ carboxylic acid or a lower ($C_1$–$C_4$) alkyl ester thereof as an additive, was found to produce substantially monomeric conjugates with excellent activity in good yield and drug loading. Preferred acids are $C_7$ to $C_{12}$ acids, and the most preferred acid is octanoic (caprylic) acid (CA).

The amount of cosolvent used is a monomeric conjugating effective amount and can be determined by those of ordinary skill in the art without undue experimentation. The amount of additive is a monomeric conjugation enhancing effective amount. This amount can also be determined by one of ordinary skill in the art without undue experimentation.

In accordance with the preferred embodiments of the present invention, additions of propylene glycol (PG) in amounts ranging from about 10% to about 60%, preferably about 10% to about 40%, and most preferably about 30% by weight of the total PBS solution and a suitable acid, and preferably caprylic acid, in amounts ranging from about 20 mM to about 100 mM, preferably from about 40 mM to about 90 mM, and most preferably about from 60 mM are added to conjugation reactions to produce substantially monomeric conjugates. Alternatively, t-butanol at concentrations ranging from about 10% and about 25% and preferably about 15% may be added. In these reactions, the concentration of MoAb ranges from about 1 to about 15 mg/ml and of the drug (AcBut calicheamicin) ranges from about 0.005 to about 1 mg/ml. The reactions are performed in PBS buffer at from about room temperature (25° C.) to about 37° C. for times ranging from about 2 hours to overnight (about 12–about 18 hours). The conjugates may be recovered and purified by, for example, HPLC or FPLC. The recovered conjugates are in substantially monomeric form and contain from about 2 to about 6 moles/mole drug/MoAb.

The addition of cosolvent and optional adjuvant may lower the pH of the PBS so that it may be necessary to adjust the pH of the solution to the preferred pH range of from about 7 to about 8.5. Most preferably, the pH of the PBS/cosolvent/optional adjuvant mixture will be about 7.7.

For various murine monoclonal antibodies, the identical conditions did not apply, but the use of combinations of propylene glycol, t-butanol, DMF, and DMSO have been found to improve drug loading and protein yield.

DESCRIPTION OF THE PREFERRED EMBODIMENTS

The present invention is further described below in specific working examples which are intended to further describe the invention without limiting the scope.

EXAMPLE 1

Conjugations in DMF: Variations in DMF concentration, drug/protein ratio and buffers employed The first set of experiments were performed on both murine and human P67.6 with variations in DMF concentrations, drug/protein ratio, and buffer. The results indicated that these "standard" conditions produce monomeric conjugate in 20–30% yield with drug loading of 1.5–3 moles drug per mole protein and therefore alternate conditions were required.

To a protein solution of 4.5–5 mg/mL protein in PBS buffer (50 mM sodium phosphate, 100 mM NaCl, pH 7.4) was added 6 molar equivalents of drug in DMF (3.3 mg/mL) with additional DMF for a final concentration of 25% DMF. This was incubated at room temperature overnight with gentle shaking. The conjugated protein was then purified by either FPLC Superose for volumes <0.5 mL and by Sephacryl S-200 for larger volumes.

For mP67.6 (large scale), this resulted in only 32% protein yield of monomer with drug loading of 1.9 M/M. For hP67.6, monomeric protein yield was 26% with drug loading of 2.9 M/M. Thus, although drug loadings on monomer were acceptable, yields were considerably below the 50% level considered minimally acceptable for further development.

A study was done to compare drug loadings vs. monomer yield in 30% DMF using hP67.6 in PBS pH 7.4, and various equivalents (5–9.5 M/M) of drug. All samples were incubated at room temperature overnight, exchanged into PBS on PD10 columns, and analyzed by spectrophotometry for protein recovery and drug loading. Samples were further analyzed by HPLC on Zorbax GF-250 in 0.2M sodium phosphate, pH 7, and Superose 12 in PBS, pH 7.4. This was followed by purification on FPLC Superose in PBS. Results: maximum loading obtainable was 3–3.5 M/M but with low yield (<20%).

A similar loading study as above was performed but with substituting HEPES buffer (100 mM, pH 7) for the PBS buffer. Results: no difference except that aggregate appeared to precipitate or stick to the column and was therefore not seen during final purification. This was followed by a loading study as above, but with 0.5M NaClO4 added to the buffer. This was done to serve as a possible solubilizing agent for the drug. Results: no obvious benefit.

An additional study was then performed in HEPES (50 mM pH 7.4) rather than PBS. Results: Again, no obvious benefit.

EXAMPLE 2

Optimization for Humanized Antibodies Experiments to Dissociate Aggregate

At this point no improvement over the initial methodology had been found. The possibility that conditions that caused a reduction in the amount of aggregate might allow increases in drug loading on purified monomer was investigated. Since all indications were that the aggregated conjugates were associative, not covalent, and probably caused by hydrophobic interactions, it was hypothesized that they could be studied alone. Thus, experiments were first performed to find additives that could break up performed aggregate. It was assumed that anything that had such activity might also serve to prevent aggregation (and thus increase yield of monomer) if used during or just after conjugation. The reagents used were chosen based on their FDA approved safety as drug additives, their potential effect for solubilizing hydrophobic moieties, and their compatibility with proteins. These studies led to the identification of three potentially useful additives.

Twelve permutations of different additives were used to disassociate aggregate. An aggregate fraction from hP67.6-AcBut purification containing ~25% dimer was concentrated to 0.7 mg/mL protein. Various additives were added to aliquots of the dimer-rich hP67.6-AcBut: PBS, 0.3M glycine, 0.2M glycine+2% maltose, 0.1M glycine+0.1M histidine, 1% Pluronic F-68, 80 mM caprylic acid (octanoic acid), 40 mM caprylic acid+6 mM N-acetyl-tryptophan, 1% benzyl alcohol, 0.5% sodium benzoate, 33% propylene glycol, and 25% glycerol. Each treated aliquot was incubated at room temperature overnight and then analyzed by gel-filtration HPLC on Zorbax GF-250 and on Superose 12 using dual detectors at 280 and 333 nm. Analysis was done for both aggregate (or dimer)-to-monomer ratio and for total recovery of monomer. Results: propylene glycol (PG), caprylic acid (CA) and glycerol were better than other additives in reducing dimer without reducing recovery of protein. They reduced aggregates by 50–90% while other additives had almost no effect.

EXAMPLE 3

Conjugations using disaggregation additives

Based on these results, PG, CA and glycerol were used during conjugation. In addition, isopropanol and t-butanol were tried as well. Isopropanol and t-butanol have been used as cosolvents at low percentages with proteins with no harm (personal observations).

Conjugation of hP67.6 to AcBut-cal was performed in the presence of 25% PG, 80 mM CA, 25% glycerol, 25% isopropanol (IPA), 25% t-butanol, or 25% PG+80 mM CA. All were done with 3.25 mg/mL protein (final) in PBS, pH 7.4, and 6 moles drug per mole MoAb. All were compared to a control conjugation performed in 25% DMF while all the test solutions contained ~5% DMF from the drug stock. Conjugation was also done with 4 M/M drug in 25% PG or 25% DMF as control. All samples were incubated at room temperature overnight, exchanged into PBS on PD10 columns, and analyzed by spectrophotometry for protein recovery and drug loading. Samples were further analyzed by HPLC on Zorbax and Superose. Following the conjugation reaction, the conjugates were purified on FPLC Superose. Results: All of these additives seemed beneficial except glycerol (low loading). PG+CA seemed best in terms of protein recovery, drug loading and minimizing aggregate.

Thus, a series of studies investigating the combination of CA to other additives, optimization of PG concentration, and direct comparisons with t-BuOH followed.

Since CA added to PG seemed to improve protein recovery, drug loading and minimize aggregation as discussed above, conjugation was performed on hP67.6 using PG, t-BuOH, or IPA (each at 25%), each with and without CA (80 mM) (to see if CA can synergize with other additives). Conditions and analysis were as above. Results: t-BuOH and CA were incompatible at these concentrations, while IPA was not as good as PG in improving yield and decreasing aggregate.

Conjugations were performed to optimize the PG+CA conditions where PG was used at 10, 15, or 20% and CA at 40 or 80 mM. Analysis was as above. Results: 20% PG and 80 mM CA appeared best, producing loading of 3–3.8 with recovery of >60%. Conclusion: t-BuOH was effective as an alternative to PG/CA and therefore more experiments were performed to confirm this observation and to optimize the conditions for t-BuOH use.

Conjugates were performed with hP67.6 in PBS using 5–20% t-BuOH and 6–10 equivalents of drug. Results: 10% t-BuOH appears sufficient with 6 equivalents of drug to produce conjugates with a loading of 2.3 M/M with little aggregate in the crude product. HEPES buffer as a substitute for PBS shows no benefit.

Conjugations were performed comparing propylene glycol (PG) at 20% and 80 mM caprylic acid (CA) vs. 15% t-BuOH. Each was tested with 6, 9, and 12 moles of drug per mole hP67.6 in PBS. Results: the combination of PG+CA seemed better in terms of protein recovery for producing higher loading, while both methods were about the same for lower loadings.

At this point, using 20% PG with 80 mM CA was a somewhat better additive than 15% t-BuOH but both were major improvements over the original conditions. However, while t-BuOH had no effect on the pH of the protein in PBS, the PG dropped the pH from 7.4 to ~6.9. This was related to the observation that the t-BuOH reactions were complete in 1–3 hours while the PG/CA reactions took overnight.

EXAMPLE 4

Conjugations in PG/CA with pH variance

A series of conjugations were performed with 30% PG/80 mM CA with and without adjustment of pH to 7.4. Also, conjugations were done using 25 vs. 30% t-BuOH, in the absence of DMF. Results: pH adjustment produced better incorporation of drug.

It was clear that conjugation in PG+CA with the pH readjusted to 7.4 produced far better yields than conjugation in t-BuOH for generating conjugates with high loading. For loadings of ~2 M/M, the two methods produced similar yields but as loadings were increased by increasing the drug/protein ratio during conjugation, yields using t-BuOH were significantly reduced to as little as 25% of the yield obtained with PG/CA (e.g. loadings of 5 M/M).

EXAMPLE 5

Large Scale Preparations

Large scale preparations (using 20–40 mg protein rather than the 0.5–1 mg per sample utilized on experimental scale) were attempted. The goal was to determine the applicability of the new conditions during scale-up and also to produce conjugates with a range of drug loading. These conjugates were tested in vivo on xenograft tumors to confirm that the additives allow production of effective conjugates and that higher loaded conjugates are more effective than lower loaded ones.

A large scale prep of hP67.6-AcBut was made (30 mg of protein used) using only 4 mole equivalents of drug and 20% PG/80 mM CA, 5% DMF, pH adjusted to 7.5. As shown below, far less aggregate was formed under these conditions than in original preparations. Final purified monomer had 1.9 M/M drug with a protein yield of 67%.

To get higher drug loading, the same conditions were followed but with 9 equivalents drug used for conjugation rather than 6. This resulted in only slightly more aggregation but yielded monomeric conjugate with 3.2 M/M drug loading and protein yield only slightly down to ~60%.

The large scale (30 mg protein) preparations, although vastly improved over initial results, still produced 30–40% less loading than expected based on the small scale work. It was suspected that the slightly increased DMF used in large scale work had caused this problem. Thus numerous small scale studies were performed over a range of DMF concentrations to confirm this.

EXAMPLE 6

Effect of small amounts of DMF during conjugation

Conjugations were performed in 10% t-BuOH with 4M/M drug while varying the DMF concentration from 1% to 7%. Here the drug stock was 10 mg/mL DMF to allow low DMF concentrations during conjugation. Results: Increasing amounts of DMF seemed to lower incorporation of drug.

Small scale conjugations were performed using 6.4 M/M drug and 30% PG/80 mM CA but using DMF at 0 and 8% vs. 25% t-BuOH with 2 and 8% DMF. Drug stocks were made in PG to better control DMF concentrations. Results: DMF was found to increase aggregation (and thus decrease monomer yield) in both PG/CA and t-BuOH (more so in PG/CA) and again PG/CA is better than t-BuOH for conjugations.

A large scale prep was performed without DMF to confirm the small scale results. Conjugation was begun at 30% PG/80 mM CA and 6.1 M/M drug. Aliquots were tested and indicated that these conditions had produced a loading of 3.2 M/M as expected based on small scale, confirming the need to avoid DMF as a cosolvent.

This conjugation was treated with an additional 3 equivalents of drug which produced a final purified monomer with a drug loading of 4.4 M/M and protein yield of 46%.

Thus, three large scale preparations had been completed to produce conjugates with drug loadings of 1.9, 3.2, and 4.4 moles drug per mole protein. These were evaluated in vitro and in vivo. The combination of PG and CA were the best reaction additives, while DMF was detrimental to the reaction.

EXAMPLE 7

Final Optimizations

A series of tests were performed to find optimal concentrations of PG and CA, optimal pH, order of addition and substitutes for DMF as drug solvents.

Small-scale conjugations were performed in 30% PG/80 mM CA but with varying orders of addition with MoAb, PG, CA, and with drug stock made up in PG, EtOH, or DMSO. Results: best order of addition is MoAb then PG then CA (adjust pH) then drug stock made up in PG. EtOH and DMSO are both acceptable alternatives to using PG for the drug stock.

A conjugation study was performed using 40, 55, 75 and 80 mM CA all with 25% PG. Results: 55 mM CA was found best in terms of protein yield and drug loading.

Again a conjugation study but with 40, 50, 60 and 70 mM CA with 25% PG. Results: 60 mM CA was found best in terms of protein yield and drug loading.

A conjugation study with 25% PG+80 mM CA and 0, 2, or 4% DMF was performed. This was to see if low levels of DMF are harmful. Results: no great differences, thus only concentrations above 4% must be problematical.

Conjugations were performed with variation in rate of stirring during conjugation. Results: no differences seen.

Conjugation was performed with drug added in EtOH instead of PG. Results: no significant change from using drug in PG.

A series of conjugations were performed in PG/CA and 6 M/M drug but with variation in pH from 7.0 to 8.5. Progress of the reaction and extent of loading was monitored by measurement of reactants and hydrolysis products (using RP-HPLC). Results: all experiments indicated that the higher the pH, the faster the reaction, ranging from 12 h at pH 7 to <45 min at pH 8.5. It was decided that a pH of >7.5 produces the highest yield and load.

The same procedure using PG/CA additives was utilized for conjugation of AcBut-Cal to two other humanized MoAbs, CT-M-01 and A33. Similar loadings and yields seen in the use of humanized P67.6 both on small and large scale was obtained for these humanized MoAbs as well.

EXAMPLE 8

Final Procedure for Humanized Antibodies

Based on all of the above results, a final procedure recommended for use in development for hP67.6 conjugation to AcBut-calicheamicin was as follows: Five stock solutions are used: hP67.6 at ~6.5 mg/mL in PBS (50 mM sodium phosphate, 100 mM NaCl, pH 7.4), propylene glycol (PG), 1M NaOH, 1M caprylic acid (CA) in PBS, pH 7.4, and drug in PG (~6 mg/mL). The final concentrations during conjugation are: 30% PG (5% of the PG is from the drug stock), 60 mMCA, approximately 4 mg/ml p67.6, and 6 moles drug per mole of hP67.6. PG is added to the hP67.6 and mixed thoroughly. The CA is added and mixed thoroughly. The pH is adjusted by addition of ~10 µL NaOH/mL of solution to obtain a pH of 7.7–7.8. Drug is then added and the solution mixed vigorously. The solution is incubated at 25° C. with shaking for 3 h followed by filtration through Millex HV filters to remove insoluble material. The conjugate is then purified by gel filtration on Sephacryl S-200 in PBS (pH 7.4) using no more than a ~1% load or, for small conjugations <0.5 mL, Superose 12 FPLC in PBS is utilized. Final monomeric (<4% dimer) conjugate is produced in >60% protein yield with a drug loading of >2.5 moles drug/mole protein.

This procedure seems to be equally effective on the three humanized MoAbs tested; A33, CT-M-01, and P67.6 which are of two different isotypes (IgG$_1$, Ig$_4$ and Ig$_4$, respectively). Thus, it is possible that this procedure will be broadly applicable to other humanized MoAbs.

EXAMPLE 9

AcBut-calicheamicin was conjugated to 5 mg of humanized C-T-MO1 monoclonal antibody in the presence of 25% propyleneglycol (PG) and 80% caprylic acid. The reaction was performed overnight (approximately 24 hours) at room temperature (25° C.). The product was analyzed by HPLC.

Results: 75% monomer produced and drug loading was 1.9 M/M

EXAMPLE 10

AcBut-calicheamicin was conjugated to 36.6 mg hC-T-MO1 monoclonal antibody in the presence of 30% PG and 60 mm CA. The reaction was performed for 2 hours at about 25° C. The product was analyzed by HPLC.

Results: 60% monomer with a drug loading of 2.2 M/M.

EXAMPLE 11

AcBut-calicheamicin was conjugated to 1 mg humanized A33 MoAb in the presence of 30% PG and 60 mm CA.

Results: Approximately 50% monomer with a drug loading of 1.8 M/M.

EXAMPLE 12

Optimization of Conditions for Murine Antibodies

The same procedures when applied to murine MoAbs are less effective. The studies described below indicate that use of the procedures for humanized MoAbs produce conjugates with lower loadings and poorer yields when applied to murine MoAbs. The results also vary greatly for each MoAb.

Conjugations using the PG/CA procedures described above produced the following loadings:

| MoAb | Loading |
| --- | --- |
| Anti-Tac | 0.7 M/M |
| M5/114 | 1.2 |
| Campath II | 1.4 |
| MN-1 | 1.2 |
| LC-1 | 1.0 |
| LK-26 | 1.2 |
| TH-69 | 1.0 |
| A33 | 1.1 |

Protein yields were poor, ranging from 20 to 40%. When mA33 was conjugated using 8 M/M drug, final loading on monomer was only 1.1–1.3 M/M. The anti-Tac conjugate, with a loading of 0.7 m/M, was reconjugated in the presence of 20% t-BuOH since that was the best backup additive. This increased loading to 2.0 M/M but in only 23% yield.

Conjugations using PG+t-BuOH:

Although the PG/CA system did not produce acceptable results with murine MoAbs, conjugation in PG followed by reconjugation in t-BuOH/(t-Bu/PG) PG seemed promising. The following studies describe conjugations in which PG and t-BuOH were used in combination. This led to the conclusion that a PG/t-BuOH system was better suited for murine MoAbs while the PG/CA system was better for humanized MoAbs.

Conjugations were performed with variations in t-BuOH and PG concentrations. It was found that PG was useful in solubilizing (clarifying) conjugation solutions for many murine MoAbs in the presence of AcBut and t-BuOH. When anti-Tac was conjugated in 20% t-BuOH, 10% PG, 6 M/M drug, the final monomer had drug loading of 1.3 M/M with a 40% yield. When done in 15% t-BuOH, 15% PG, 6.7 M/M drug, the product had drug loading of 1.4 M/M and a 50% yield, a slight improvement over the previous attempt but distinctly better than the 0.7 M/M loading and ~20% yield obtained in PG/CA. When the same conditions were followed but with protein concentration increased to 2.8 mg/mL (from ~2) final drug loading increased to 2.2 M/M.

For mA33, no conditions were found that could bring loading significantly above 1.0 M/M but the above combination of t-BuOH and PG (with 8 M/M drug) produced conjugate in 60% yield even on large scale. Three IgG$_1$ murine MoAbs (that would presumably have similar chemical reactivities) MOPC, M44, and M67, when conjugated under essentially identical conditions (15% t-BuOH, 10–20% PG, 6.7 M/M drug) all produced monomer with loading ~1.0, but in yields ranging from 14–45%. For MOPC, increasing protein concentration to 2.8 mg/mL (as with anti-Tac) and using 8 M/M drug in the 15% t-BuOH, 20% PG buffer system increased drug loading to 1.7 M/M in ~50% yield.

Final Procedure for Murine Antibodies

Based on this series of conjugations, the recommended procedure for conjugation of murine MoAbs is substantially different than that for humanized MoAbs. Additionally, the optimized protein yields and drug loadings obtained vary considerably among the different murine MoAbs tested in contrast with the combined observations from the three humanized MoAbs studied.

Again, PBS, pH 7.4, is utilized as the buffer but the MoAb stock is at 4 to 5.5 mg/mL, t-BuOH is used as an additional cosolvent (but not CA), and the drug stock (8–10 mg/mL) is made in DMSO (or DMF). Final reaction conditions are 15% t-BuOH, ~20% propylene glycol (or more if needed to clarify the solution), 2–4% DMSO (from the drug stock), and 6–8 moles drug/mole protein. The conjugation proceeds for 3–20 h, incubated at 25° C. with shaking. Purification is as described above for humanized conjugates. Final protein yields range from 25 to 60% and drug loading from 1 to 2.2 moles of drug per mole of MoAb, depending on the individual MoAb.

All patents, applications, articles, publications, and test methods mentioned herein are hereby incorporated by reference.

Many variations of the present invention will suggest themselves to those skilled in the art in light of the above detailed description. Such obvious variations are within the full intended scope of the appended claims.

What is claimed is:

1. A method for preparing monomeric calicheamicin derivative/carrier conjugates with higher drug loading/yield and decreased aggregation having the formula,

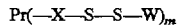

wherein:

Pr is a proteinaceous carrier,

X is a linker that comprises a product of any reactive group that can react with a proteinaceous carrier, W is the calicheamicin residue formed when a calicheamicin is cleaved at a methyl trisulfide linkage, and m is from 0.1 to 15;

said method comprising the steps of:

(1) incubating a calicheamicin derivative (X—S—S—W) and a proteinaceous carrier (Pr) in a phosphate buffered solution which solution further comprises (a) a cosolvent comprising propylene glycol, and (b) an additive comprising at least one C$_6$–C$_{25}$ carboxylic acid, wherein the incubation is conducted at a temperature ranging from about 25° C. to about 37° C. for a period of time ranging from about 2 hours to about 18 hours to produce a calicheamicin derivative/carrier conjugate; and (2) purifying the calicheamicin derivative/carrier conjugate produced in step (1) to produce a monomeric calicheamicin derivative/carrier conjugate.

2. The method of claim 1, wherein X has the formula Z—Sp wherein:

Sp is a straight or branched-chain divalent or trivalent (C$_1$–C$_{18}$) radical, divalent or trivalent aryl or heteroaryl radical, divalent or trivalent (C$_3$–C$_{18}$) cycloalkyl or heterocycloalkyl radical, divalent or trivalent aryl- or heteroaryl-aryl (C$_1$–C$_{18}$) radical, divalent or trivalent cycloalkyl- or heterocycloalkyl-alkyl (C$_1$–C$_{18}$) radical or divalent or trivalent (C$_2$–C$_{18}$) unsaturated alkyl radical, wherein when Sp is a trivalent radical, Sp can be additionally substituted by amino, alkylamino, arylamino, heteroarylamino, carboxyl, lower alkoxy, hydroxy, thiol, or lower alkylthio groups; and Z is —CONH, —CONHN=CH—, —CONHNHCH$_2$—, —NHCONHN=CH—, —NHCONHNHCH$_2$—, —NHCSNHN=CH—, —NHCH$_2$—, —N=CH—, —CO$_2$—, —NHCH$_2$CO$_2$—, —S—S—,

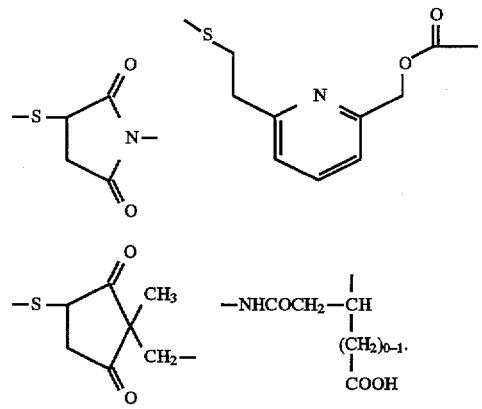

3. The method of claim 1, wherein X has the formula

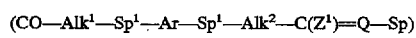

wherein

Alk$^1$ and Alk$^2$ are independently a bond or branched or unbranched (C$_1$–C$_{10}$) alkylene chain;

Sp$^1$ is a bond, —S—, —O—, —CONH—, —NHCO—, —NR'—, —N(CH$_2$CH$_2$)$_2$N—, or —X—Ar'—Y—(CH$_2$)$_n$—Z wherein X, Y, and Z are independently a bond, —NR'—, —S—, or —O—, with the proviso that when n=0, then at least one of Y and Z must be a bond, and Ar' is 1,2-, 1,3-, or 1,4-phenylene optionally substituted with one, two, or three groups of (C$_1$–C$_5$) alkyl, (C$_1$–C$_4$) alkoxy, (C$_1$–C$_4$) thioalkoxy, halogen, nitro, —COOR', —CONHR', —(CH$_2$)$_n$COOR', —S(CH$_2$)$_n$COOR', —O(CH$_2$)$_n$CONHR', or —S(CH$_2$)$_n$CONHR', with the proviso that when Alk$^1$ is a bond, Sp$^1$ is a bond;

n is an integer from 0 to 5;

R' is a branched or unbranched (C$_1$–C$_5$) chain optionally substituted by one or two groups of —OH, (C$_1$–C$_4$)

alkoxy, ($C_1$–$C_4$) thioalkoxy, halogen, nitro, ($C_1$–$C_3$) dialkylamino, or ($C_1$–$C_3$) trialkylammonium-$A^-$ where $A^-$ is a pharmaceutically acceptable anion completing a salt;

Ar is 1,2-, 1,3-, or 1,4-phenylene optionally substituted with one, two, or three groups of ($C_1$–$C_6$) alkyl, ($C_1$–$C_4$) alkoxy, ($C_1$–$C_4$) thioalkoxy, halogen, nitro, —COOR', —CONHR', —O($CH_2$)$_n$COOR', —S($CH_2$)$_n$COOR', —O($CH_2$)$_n$CONHR', or —S($CH_2$)$_n$CONHR' wherein n and R' are as defined above or a 1,2-, 1,3-, 1,4-, 1,5-, 1,6-, 1,7-, 1,8-, 2,3-, 2,6-, or 2,7-naphthylidene or

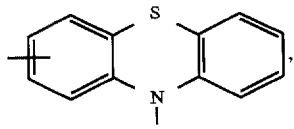

each naphthylidene or phenothiazine optionally substituted with one, two, three, or four groups of ($C_1$–$C_6$) alkyl, ($C_1$–$C_5$) alkoxy, ($C_1$–$C_4$) thioalkoxy, halogen, nitro, —COOR', —CONHR', —O($CH_2$)$_n$COOR', —S($CH_2$)$_n$COOR', or —S($CH_2$)$_n$CONHR' wherein n and R' are as defined above, with the proviso that when Ar is naphthylidene, $Z^1$ is not hydrogen and with the proviso that when Ar is phenothiazine, $Sp^1$ is a bond only connected to nitrogen;

$Sp^2$ is a bond, —S—, or —O—, with the proviso that when $Alk^2$ is a bond, $Sp^2$ is a bond;

$Z^1$ is H, ($C_1$–$C_5$) alkyl, or phenyl optionally substituted with one, two, or three groups of ($C_1$–$C_5$) alkyl, ($C_1$–$C_5$) alkoxy, ($C_1$–$C_4$) thioalkoxy, halogen, nitro, —COOR', —CONHR', —O($CH_2$)$_n$COOR', —S($CH_2$)$_n$COOR', —O($CH_2$)$_n$CONHR', or —S($CH_2$)$_n$CONHR' wherein n and R' are as above;

Sp is a straight or branched-chain divalent or trivalent ($C_1$–$C_{18}$) radical, divalent or trivalent aryl or heteroaryl radical, divalent or trivalent ($C_3$–$C_{18}$) cycloalkyl or heterocycloalkyl radical, divalent or trivalent aryl- or heteroaryl-aryl ($C_1$–$C_{18}$) radical, divalent or trivalent cycloalkyl- or heterocycloalkyl-alkyl ($C_1$–$C_{18}$) radical or divalent or trivalent ($C_2$–$C_{18}$) unsaturated alkyl radical, wherein heteroaryl is furyl, thienyl, N-methylpyrrolyl, pyridinyl, N-methylimidazolyl, oxazolyl, pyrimidinyl, quinolyl, isoquinolyl, N-methylcarbazoyl, aminocoumarinyl, or phenazinyl and wherein when Sp is a trivalent radical, Sp can be additionally substituted by lower ($C_1$–$C_5$) dialkylamino, lower ($C_1$–$C_5$) alkoxy, hydroxy, or lower ($C_1$–$C_5$) alkylthio groups; and Q is =NHNCO—, =NHNCS—, =NHNCONH—, =NHNCSNH—, or =NHO—.

4. The method of claim 3, wherein

Sp' is a bond, —S—, —O—, —CONH—, —NHCO—, or —NR'—, with the proviso that when $Alk^1$ is a bond, $Sp^1$ is a bond;

Ar is 1,2-, 1,3-, or 1,4-phenylene optionally substituted with one, two, or three groups of ($C_1$–$C_6$) alkyl, ($C_1$–$C_5$) alkoxy, ($C_1$–$C_4$) thioalkoxy, halogen, nitro, —COOR', —CONHR', —O($CH_2$)$_n$COOR', —S($CH_2$)$_n$COOR', —O($CH_2$)$_n$CONHR', or —S($CH_2$)$_n$CONHR' or Ar is a 1,2-, 1,3-, 1,4-, 1,5-, 1,6-, 1,7-, 1,8-, 2,3-, 2,6-, or 2,7- naphthylidene each optionally substituted with one, two, three, or four groups of ($C_1$–$C_6$) alkyl, ($C_1$–$C_5$) alkoxy, ($C_1$–$C_4$) thioalkoxy, halogen, nitro, —COOR', —CONHR', —O($CH_2$)$_n$COOR', —S($CH_2$)$_n$COOR', —O($CH_2$)$_n$CONHR', or —S($CH_2$)$_n$CONHR';

$Alk^2$ is a branched or unbranched ($C_1$–$C_{10}$) alkylene chain;

$Z^1$ is phenyl optionally substituted with one, two, or three groups of ($C_1$–$C_5$) alkyl, ($C_1$–$C_4$) alkoxy, ($C_1$–$C_4$) thioalkoxy, halogen, nitro, —COOR', —CONHR', —O($CH_2$)$_n$COOR', —S($CH_2$)$_n$COOR', —O($CH_2$)$_n$CONHR', or —S($CH_2$)$_n$CONHR'; and $Alk^2$ and $Sp^2$ are together a bond.

5. The method of claim 1, wherein the phosphate buffered solution of step (1) has a pH in a range from about 7.0 to 8.5.

6. The method of claim 1, wherein the calicheamicin derivative of step (1) comprises a gamma calicheamicin derivative.

7. The method of claim 6, wherein the calicheamicin derivative is present in step (1) in an amount ranging from about 0.005 mg/ml to about 1.0 mg/ml.

8. The method of claim 1, wherein X is 4(4(acetyl) phenoxy) butanoic acid.

9. The method of claim 1, wherein the proteinaceous carrier comprises a humanized monoclonal antibody.

10. The method of claim 9, wherein the humanized monoclonal antibody is present in step (1) in an amount ranging from about 1 mg/ml to about 15 mg/ml.

11. The method of claim 1, wherein the cosolvent propylene glycol of step (1) is present in an amount ranging from about 10% to about 60% by weight of the total phosphate buffered solution.

12. The method of claim 1, wherein the additive of step (1) is present in an amount ranging from 20 to 100 mM.

13. The method of claim 12, wherein the additive of step (1) comprises octanoic acid.

14. The method of claim 1, wherein the cosolvent propylene glycol of step (1) is present in an amount of 30% by weight of the total phosphate buffered solution and the additive of step (1) comprises octanoic acid in an amount of 60 mM.

15. A method for preparing monomeric calicheamicin derivative/carrier conjugates with higher drug loading/yield and decreased aggregation having the formula,

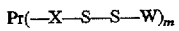

wherein:

Pr is a proteinaceous carrier,

X is a linker that comprises a product of any reactive group that can react with a proteinaceous carrier, W is the calicheamicin residue formed when a calicheamicin is cleaved at a methyl trisulfide linkage; and m is from 0.1 to 15, said method comprising the steps of:

(1) incubating a calicheamicin derivative (X—S—S—W) and a proteinaceous carrier (Pr) in a phosphate buffered solution which solution further comprises a cosolvent t-butanol, wherein the incubation is conducted at a temperature ranging from about 25° C. to about 37° C. for a period of time ranging from about 2 hours to about 18 hours to produce a calicheamicin derivative/carrier conjugate; and (2) purifying the calicheamicin derivative/carrier conjugate produced in step (1) to produce a monomeric calicheamicin derivative/carrier conjugate.

16. The method of claim 15, wherein X has the formula Z—Sp wherein:

Sp is a straight or branched-chain divalent or trivalent (C₁-C₁₈) radical, divalent or trivalent aryl or heteroaryl radical, divalent or trivalent (C₃-C₁₈) cycloalkyl or heterocycloalkyl radical, divalent or tdvalent aryl- or heteroaryl-aryl (C₁-C₁₈) radical, divalent or trivalent cycloalkyl- or heterocycloalkyl-alkyl (C₁-C₁₈) radical or divalent or trivalent (C₂-C₁₈) unsaturated alkyl radical, wherein when Sp is a trivalent radical, Sp can be additionally substituted by amino, alkylamino, arylamino, heteroarylamino, carboxyl, lower alkoxy, hydroxy, thiol, or lower alkylthio groups; and Z is —CONH—, —CONHN=CH—, —CONHNHCH₂—, —NHCONHN=CH—, —NHCONHNHCH₂—, —NHCSNHN=CH—, —NHCH₂—, —N=CH—, —CO₂—, —NHCH₂CO₂—, —S—S—,

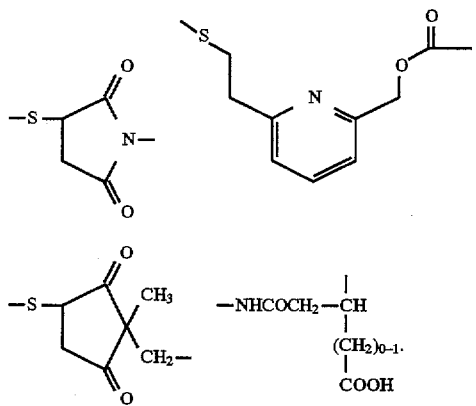

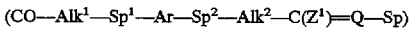

17. The method of claim 15, wherein X has the formula (CO—Alk¹—Sp¹—Ar—Sp²—Alk²—C(Z¹)=Q—Sp)

wherein

Alk¹ and Alk² are independently a bond or branched or unbranched (C₁-C₁₀) alkylene chain;

Sp¹ is a bond, —S—, —O—, —CONH—, —NHCO—, —NR'—, —N(CH₂CH₂)₂N—, or —X—Ar'—Y—(CH₂)ₙ—Z wherein X, Y, and Z are independently a bond, —NR'—, —S—, or —O—, with the proviso that when n=0, then at least one of Y and Z must be a bond, and Ar' is 1,2-, 1,3-, or 1,4-phenylene optionally substituted with one, two, or three groups of (C₁-C₅) alkyl, (C₁-C₄) alkoxy, (C₁-C₄) thioalkoxy, halogen, nitro, —COOR', —CONHR', —O(CH₂)ₙCOOR', —S(CH₂)ₙCOOR', —O(CH₂)ₙCONHR', or —S(CH₂)ₙCONHR', with the proviso that when Alk¹ is a bond, Sp¹ is a bond;

n is an integer from 0 to 5;

R' is a branched or unbranched (C₁-C₅) chain optionally substituted by one or two groups of —OH, (C₁-C₄) alkoxy, (C₁-C₄) thioalkoxy, halogen, nitro, (C₁-C₃) dialkylamino, or (C₁-C₃) trialkylammonium-A⁻ where A⁻ is a pharmaceutically acceptable anion completing a salt;

Ar is 1,2-, 1,3-, or 1,4-phenylene optionally substituted with one, two, or three groups of (C₁-C₆) alkyl, (C₁-C₄) alkoxy, (C₁-C₄) thioalkoxy, halogen, nitro, —COOR', —CONHR', —O(CH₂)ₙCOOR', —S(CH₂)ₙCOOR', —O(CH₂)ₙCONHR', or —S(CH₂)ₙCONHR' wherein n and R' are as defined above or a 1,2-, 1,3-, 1,4-, 1,5-, 1,6-, 1,7-, 1,8-, 2,3-, 2,6-, or 2,7- naphthylidene or

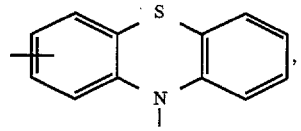

each naphthylidene or phenothiazine optionally substituted with one, two, three, or four groups of (C₁-C₆) alkyl, (C₁-C₅) alkoxy, (C₁-C₄) thioalkoxy, halogen, nitro, —COOR', —CONHR', —O(CH₂)ₙCOOR', —S(CH₂)ₙCOOR', or —S(CH₂)ₙCONHR' wherein n and R' are as defined above, with the proviso that when Ar is naphthylidene, Z¹ is not hydrogen and with the proviso that when Ar is phenothiazine, Sp¹ is a bond only connected to nitrogen;

Sp² is a bond, —S—, or —O—, with the proviso that when Alk² is a bond, Sp² is a bond;

Z¹ is H, (C₁-C₅) alkyl, or phenyl optionally substituted with one, two, or three groups of (C₁-C₅) alkyl, (C₁-C₅) alkoxy, (C₁-C₄) thioalkoxy, halogen, nitro, —COOR', —CONHR', —O(CH₂)ₙCOOR', —S(CH₂)ₙCOOR', —O(CH₂)ₙCONHR', or —S(CH₂)ₙCONHR', wherein n and R' are as above;

Sp is a straight or branched-chain divalent or trivalent (C₁-C₁₈) radical, divalent or trivalent aryl or heteroaryl radical, divalent or trivalent (C₃-C₁₈) cycloalkyl or heterocycloalkyl radical, divalent or trivalent aryl- or heteroaryl-aryl (C₁-C₁₈) radical, divalent or trivalent cycloalkyl- or heterocycloalkyl-alkyl (C₁-C₁₈) radical or divalent or trivalent (C₂-C₁₈) unsaturated alkyl radical, wherein heteroaryl is furyl, thienyl, N-methylpyrrolyl, pyridinyl, N-methylimidazolyl, oxazolyl, pyrimidinyl, quinolyl, isoquinolyl, N-methylcarbazoyl, aminocoumarinyl, or phenazinyl and wherein when Sp is a trivalent radical, Sp can be additionally substituted by lower (C₁-C₅) dialkylamino, lower (C₁-C₅) alkoxy, hydroxy, or lower (C₁-C₅) alkylthio groups; and Q is =NHNCO—, =NHNCS—, =NHNCONH—, =NHNCSNH—, or =NHO—.

18. The method of claim 17, wherein

Sp' is a bond, —S—, —O—, —CONH—, —NHCO—, or —NR'—, with the proviso that when Alk¹ is a bond, Sp¹ is a bond;

Ar is 1,2-, 1,3-, or 1,4-phenylene optionally substituted with one, two, or three groups of (C₁-C₆) alkyl, (C₁-C₅) alkoxy, (C₁-C₄) thioalkoxy, halogen, nitro, —COOR', —CONHR', —O(CH₂)ₙCOOR', —S(CH₂)ₙCOOR', —O(CH₂)ₙCONHR', or —S(CH₂)ₙCONHR' or Ar is a 1,2-, 1,3-, 1,4-, 1,5-, 1,6-, 1,7-, 1,8-, 2,3-, 2,6-, or 2,7- naphthylidene each optionally substituted with one, two, three, or four groups of (C₁-C₆) alkyl, (C₁-C₅) alkoxy, (C₁-C₄) thioalkoxy, halogen, nitro, —COOR', —CONHR', —O(CH₂)ₙCOOR', —S(CH₂)ₙCOOR', —O(CH₂)ₙCONHR', or —S(CH₂)ₙCONHR';

Alk² is a branched or unbranched (C₁-C₁₀) alkylene chain;

Z¹ is phenyl optionally substituted with one, two, or three groups of (C₁-C₅) alkyl, (C₁-C₄) alkoxy, (C₁-C₄) thioalkoxy, halogen, nitro, —COOR', —CONHR', —O(CH₂)ₙCOOR', —S(CH₂)ₙCOOR', —O(CH₂)ₙCONHR', or —S(CH₂)ₙCONHR'; and Alk² and Sp² are together a bond.

19. The method of claim 15, wherein the phosphate buffered solution of step (1) has a pH in a range from about 7.0 to 8.5.

20. The method of claim 15, wherein the calicheamicin derivative of step (1) comprises a gamma calicheamicin derivative.

21. The method of claim 20, wherein the calicheamicin derivative is present in step (1) in an amount ranging from about 0.005 mg/ml to about 1.0 mg/ml.

22. The method of claim 15, wherein X is 4(4(acetyl) phenoxy) butanoic acid.

23. The method of claim 15, wherein the proteinaceous carrier comprises a humanized monoclonal antibody.

24. The method of claim 23, wherein the humanized monoclonal antibody is present in step (1) in an amount ranging from about 1 mg/ml to about 15 mg/ml.

25. The method of claim 15, wherein the t-butanol is present in step (1) in an amount ranging from about 10% to about 25% of the phosphate buffered solution.

26. The method of claim 15, wherein the t-butanol is present in step (1) in an amount of 15% of the phosphate buffered solution.

27. A method for preparing monomeric calicheamicin derivative/carrier conjugates with higher drug loading/yield and decreased aggregation having the formula,

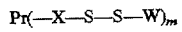

wherein:

Pr is a murine monoclonal antibody,

X is a linker that comprises a product of any reactive group that can react with Pr, W is the calicheamicin residue formed when a calicheamicin is cleaved at a methyl trisulfide linkage, and m is from 0.1 to 15;

said method comprising the steps of:

(1) incubating a calicheamicin derivative (X—S—S—W) and a murine monoclonal antibody (Pr) in a phosphate buffered solution which solution further comprises cosolvents propylene glycol and t-butanol, wherein the incubation is conducted at a temperature ranging from about 25° C. to about 37° C. for a period of time ranging from about 3 hours to about 20 hours to produce a calicheamicin derivative/carrier conjugate; and (2) purifying the calicheamicin derivative/carrier conjugate produced in step (1) to produce a monomeric calicheamicin derivative/carrier conjugate.

28. The method of claim 27, wherein the cosolvent propylene glycol is present in an amount of 20% of the phosphate buffered solution and the cosolvent t-butanol is present in an amount of 15% of the phosphate buffered solution.

29. The method of claim 27, wherein the solution of step (1) further comprises DMSO or DMF as a third cosolvent.

30. The method of claim 29, wherein the cosolvent DMSO or DMF is present in an amount of 2 to 4% of the phosphate buffered solution.

* * * * *